United States Patent
Makin et al.

(10) Patent No.: US 11,963,839 B2
(45) Date of Patent: Apr. 23, 2024

(54) DENTAL MONITORING SYSTEM

(71) Applicant: A.T. STILL UNIVERSITY, Kirksville, MO (US)

(72) Inventors: Inder Raj S. Makin, Mesa, AZ (US); Harry Jabs, Oakland, CA (US); Shervin Tony Hashemian, Scottsdale, AZ (US)

(73) Assignee: A. T. STILL UNIVERSITY, Kirksville, MO (US)

( * ) Notice: Subject to any disclaimer, the term of this patent is extended or adjusted under 35 U.S.C. 154(b) by 829 days.

(21) Appl. No.: 16/060,667

(22) PCT Filed: Jan. 10, 2018

(86) PCT No.: PCT/US2018/013106
§ 371 (c)(1),
(2) Date: Jun. 8, 2018

(87) PCT Pub. No.: WO2018/132435
PCT Pub. Date: Jul. 19, 2018

(65) Prior Publication Data
US 2021/0161633 A1    Jun. 3, 2021

Related U.S. Application Data (60) Provisional application No. 62/444,676, filed on Jan. 10, 2017.

(51) Int. Cl.
*A61C 19/04*    (2006.01)
*A61B 5/00*    (2006.01)
(Continued)

(52) U.S. Cl.
CPC .............. *A61C 19/04* (2013.01); *A61B 5/002* (2013.01); *A61B 5/14507* (2013.01);
(Continued)

(58) Field of Classification Search
CPC ........... A61C 19/04; A61C 8/00; A61B 5/002; A61B 5/14507; A61B 5/1477;
(Continued)

(56) References Cited

U.S. PATENT DOCUMENTS 4,319,578 A    3/1982   Enger
4,629,424 A    12/1986  Lauks et al.
(Continued)

FOREIGN PATENT DOCUMENTS

WO    2016144873 A3    11/2016

OTHER PUBLICATIONS

International Search Report and Written Opinion issued in corresponding International Application No. PCT/US2018/013106, dated Mar. 29, 2018, 12 pages.
(Continued)

*Primary Examiner* — May A Abouelela
(74) *Attorney, Agent, or Firm* — Quarles & Brady LLP (57) ABSTRACT

A dental monitoring system comprises a intra-oral insert configured to be received in the mouth of a subject; a sensor connected to the intra-oral insert and in electrical communication with a controller having a non-volatile memory; a transponder coil received in the intra-oral insert and in electrical communication with the controller; and a transceiver coil in selective wireless electrical communication with the transponder coil. The selective wireless communication between the transponder coil and the transceiver coil is provided by near-field communication.

23 Claims, 9 Drawing Sheets

(51) Int. Cl.
*A61B 5/145* (2006.01)
*A61B 5/1477* (2006.01)

(52) U.S. Cl.
CPC .......... *A61B 5/1477* (2013.01); *A61B 5/6815* (2013.01); *A61B 5/682* (2013.01); *A61B 5/14539* (2013.01); *A61B 2560/0214* (2013.01); *A61B 2562/0247* (2013.01)

(58) Field of Classification Search
CPC ... A61B 5/6815; A61B 5/682; A61B 5/14539; A61B 2560/0214; A61B 2562/0247; A61B 5/0004; A61B 5/0015; A61B 5/0026; A61B 5/0031; A61B 5/4277; A61B 5/228; A61B 5/4542–4557; G01N 27/4167
See application file for complete search history.

(56) References Cited

U.S. PATENT DOCUMENTS

| | | | |
|---|---|---|---|
| 5,078,153 A * | 1/1992 | Nordlander | A61B 5/228 600/595 |
| 6,869,588 B2 | 3/2005 | Weller et al. | |
| 8,712,078 B2 | 4/2014 | Abolfathi | |
| 8,771,149 B2 | 7/2014 | Rahman et al. | |
| 8,944,813 B2 | 2/2015 | Kotlarchik | |
| 10,135,076 B1 * | 11/2018 | Liu | A61B 5/6821 |
| 2005/0177069 A1 * | 8/2005 | Takizawa | A61B 5/0084 600/573 |
| 2005/0266074 A1 * | 12/2005 | Zilberstein | A61B 1/00156 424/464 |
| 2007/0106138 A1 * | 5/2007 | Beiski | A61B 5/682 600/549 |
| 2008/0001735 A1 * | 1/2008 | Tran | A61B 5/0022 340/539.22 |
| 2008/0214966 A1 * | 9/2008 | Slayton | A61N 7/02 601/3 |
| 2010/0168805 A1 * | 7/2010 | Colin | A61N 1/36034 607/2 |
| 2010/0179541 A1 | 7/2010 | Joseph et al. | |
| 2011/0159566 A1 | 6/2011 | Josephson et al. | |
| 2011/0207990 A1 * | 8/2011 | Mersky | H04R 25/554 381/151 |
| 2011/0218455 A1 * | 9/2011 | Hennig | A61B 5/0053 600/553 |
| 2011/0295083 A1 * | 12/2011 | Doelling | A61B 5/11 600/407 |
| 2012/0172677 A1 | 7/2012 | Logan et al. | |
| 2012/0172679 A1 * | 7/2012 | Logan | A61B 5/01 600/301 |
| 2012/0209086 A1 * | 8/2012 | Beute | A61B 5/7285 600/479 |
| 2013/0172691 A1 * | 7/2013 | Tran | A61B 5/0022 600/595 |
| 2013/0211270 A1 * | 8/2013 | St. Laurent | A61B 5/08 600/595 |
| 2014/0074179 A1 * | 3/2014 | Heldman | G16H 50/50 607/45 |
| 2014/0099594 A1 * | 4/2014 | Li | A61C 1/0015 433/216 |
| 2014/0114165 A1 * | 4/2014 | Walker | A61B 3/113 600/383 |
| 2014/0134561 A1 | 5/2014 | Smith et al. | |
| 2014/0199650 A1 * | 7/2014 | Moffson | B65D 51/245 600/409 |
| 2014/0257051 A1 * | 9/2014 | Cam | A61B 5/0004 600/595 |
| 2015/0112173 A1 * | 4/2015 | Yao | A61B 5/742 156/303.1 |
| 2015/0112175 A1 * | 4/2015 | Yao | A61B 5/1486 264/1.7 |
| 2015/0148705 A1 * | 5/2015 | Baym | A61B 90/98 600/572 |
| 2015/0305671 A1 * | 10/2015 | Yoon | A61B 5/01 600/28 |
| 2016/0015321 A1 | 1/2016 | Hashemian | |
| 2016/0022398 A1 * | 1/2016 | Vetter | A61B 5/053 433/27 |
| 2016/0045160 A1 | 2/2016 | Keating et al. | |
| 2016/0058315 A1 * | 3/2016 | Wiser | A61B 5/6821 600/479 |
| 2016/0066776 A1 | 3/2016 | Weiss et al. | |
| 2016/0113495 A1 * | 4/2016 | Nanjundappa | A61B 1/00016 433/29 |
| 2016/0184050 A1 * | 6/2016 | Chodorow | A61C 8/0089 433/29 |
| 2016/0242632 A1 * | 8/2016 | Lu | A61B 5/037 |
| 2016/0310077 A1 * | 10/2016 | Hunter | A61F 5/055 |
| 2016/0317095 A1 * | 11/2016 | Berger | A61B 5/6862 |
| 2016/0338626 A1 | 11/2016 | Wang et al. | |
| 2016/0338646 A1 * | 11/2016 | Lee | A61B 5/0022 |
| 2016/0367188 A1 | 12/2016 | Malik et al. | |
| 2016/0374609 A1 * | 12/2016 | Vetter | A46B 15/0012 433/27 |
| 2017/0020391 A1 * | 1/2017 | Flitsch | G16H 40/67 |
| 2017/0024555 A1 * | 1/2017 | Flitsch | H04L 67/12 |
| 2017/0056146 A1 * | 3/2017 | Boughorbel | A61B 5/0031 |
| 2017/0116665 A1 * | 4/2017 | Alzahrani | A46B 5/0025 |
| 2017/0234818 A1 * | 8/2017 | Jesme | G01N 27/18 374/54 |
| 2017/0252140 A1 * | 9/2017 | Murphy | A61B 5/4833 |
| 2018/0014782 A1 * | 1/2018 | Marcus | A61B 5/11 |
| 2018/0103899 A1 * | 4/2018 | Cahan | G01L 5/1627 |
| 2018/0153450 A1 * | 6/2018 | Routh | A61B 5/7445 |
| 2018/0214054 A1 * | 8/2018 | Soltani | A61B 5/1473 |
| 2018/0310881 A1 * | 11/2018 | Yoon | A61B 5/02416 |

OTHER PUBLICATIONS

Braschler et al. "Fluidic microstructuring of alginate hydrogels for the single cell niche" The Royal Society of Chemistry 2010 Lab Chip, 2010, 10, pp. 2771-2777.

* cited by examiner

DENTAL MONITORING SYSTEM

CROSS-REFERENCE TO RELATED APPLICATIONS

This application represents the U.S. National Stage of International Application No. PCT/US2018/013106, filed Jan. 10, 2018 which claims priority to U.S. Provisional Patent Application No. 62/444,676 entitled "Dental Monitoring System" filed Jan. 10, 2017, which is hereby incorporated by reference in its entirety.

STATEMENT REGARDING FEDERALLY SPONSORED RESEARCH

Not Applicable.

BACKGROUND OF THE INVENTION

1. Field of the Disclosure

This disclosure relates to a dental monitoring system for monitoring dental parameters of a subject.

2. Description of the Related Art

The oral cavity of the human body naturally produces saliva to facilitate the breakdown of food during mastication. The saliva produced in the oral cavity may experience significant changes in physical and biochemical properties. Changes in physical and biochemical properties within the oral cavity may significantly affect overall health including causing an increase in tooth decay and the formation of dental cavities. In some cases, pH levels within the oral cavity are of particular interest to health practitioners in order to monitor the oral health of patients.

What is needed therefore is a dental monitoring system capable of monitoring the physical and biochemical properties within the oral cavity of a patient.

SUMMARY OF THE INVENTION

In one embodiment of the disclosure, a dental monitoring system is provided. The dental monitoring system comprises an intra-oral insert configured to be received in the mouth of a subject; one or more sensors connected to the intra-oral insert and in electrical communication with a controller having a non-volatile memory; a transponder coil received in the intra-oral insert and in electrical communication with the controller; and a transceiver coil in selective wireless electrical communication with the transponder coil. The selective wireless communication between the transponder coil and the transceiver coil can be provided by near-field communication.

In some embodiments, the dental monitoring system comprises a support frame configured to mount the transceiver coil. The support frame can be structured to loop around at least a portion of an ear of the subject. The support frame can be dimensioned such that the transceiver coil is positioned adjacent to a cheek of the subject. At least one of the one or more sensors can be a pH sensor, a biochemical sensor, or a pressure sensor, and the controller can comprise a microcontroller and a JTAG programming port. Near-field communication can communicate power from the transceiver coil to the transponder coil and it can simultaneously communicate data bi-directionally, for example through impedance modulation.

In some embodiments, the dental monitoring system can further comprise an adhesive patch that retains the transceiver coil on the cheek of the subject. The adhesive patch can be worn for an extended period of time thereby providing continuous monitoring over the extended period of time.

In some embodiments, at least one of the one or more sensors may be a biochemical sensor and at least one of the one or more sensors is a pressure sensor. In some embodiments, a plurality of the one or more sensors may be positioned on an inner recessed area disposed between a raised outer profile and a raised inner profile of the intra-oral insert. A plurality of the one or more sensors may be positioned on both sides of a raised outer profile that extends from an inner recessed area disposed between a raised inner profile and the raised outer profile of the intra-oral insert. A plurality of the one or more sensors may be positioned on a raised inner profile that extends from an inner recessed area disposed between the raised inner profile and the raised outer profile of the intra-oral insert.

In another embodiment, a dental monitoring system is provided. The dental monitoring system may comprise an intra-oral insert configured to be received in the mouth of a subject; a plurality of sensors connected to the intra-oral insert and in electrical communication with a controller having a non-volatile memory, the plurality of sensors configured to monitor one or more parameters of pressure, force, shear force, acceleration, velocity, pH, and temperature; a transponder coil received in the intra-oral insert and in electrical communication with the controller; and a transceiver coil in selective wireless electrical communication with the transponder coil, the transceiver coil selectively powering the transponder coil. The selective wireless communication between the transponder coil and the transceiver coil can be provided by near-field communication. The controller can be configured to communicate a command to the plurality of sensors to generate a data reading. The controller can communicate the data reading to a smart device configured to process, display and log the data reading on a graphical user interface and to a mass storage media, respectively. The NFC communication may be configured to use encryption for data security.

In another embodiment, a method of dental monitoring is provided. The method of dental monitoring can include the steps of: (i) inserting the intra-oral insert into the mouth of a subject; (i) energizing the transponder coil by the transceiver coil to power the intra-oral insert circuitry; (ii) sensing a parameter of the subject using a sensor connected to the intra-oral insert; (iii) communicating the sensed parameter to a controller having a non-volatile memory; (iv) communicating the sensed parameter from the controller to a transponder coil received in the intra-oral insert; and (v) communicating the sensed parameter wirelessly from the transponder coil to a transceiver coil using near-field communication. In some embodiments, the parameter of the subject is sensed when the subject initiates a force to the sensor. The parameter of the subject can be a pH level. In other embodiments, the parameter can be temperature, pressure, moisture, light, total dissolved solids, ionic strength, conductivity, dissolved oxygen, oxidation-reduction potential or any combination of parameters. In yet other embodiments, the parameter can be the sensing of a biochemical species, such as with an ion-selective chem-FET (chemical field effect transistor).

To accurately assess a variety of dental and oral conditions in a subject, it is beneficial for a dental practitioner to monitor as many physiological, physical and biochemical parameters as possible. Ideally, these parameters are continuously monitored and logged in real-time to show trending over time. To maintain patient comfort, any instrumentation must be designed to be as least invasive as possible while still providing the required parameter readout. To assure safety, any instrumentation placed into the oral cavity must be physically large enough not to risk accidental swallowing. Alternatively, any instrumentation placed into the oral cavity must be provided with a means to securely anchor it to structures such as teeth, gums or other tissue. The presented dental monitoring system concept addresses these requirements.

Sensors and associated electronics must be as small as possible to fit into the oral cavity without causing patient discomfort. Many electronic chips available today are as small as a grain of rice, immediately raising the concern of accidental swallowing. Therefore, all instrumentation components will be mounted to a large framework, such as an athletic intra-oral insert or an anti-snore piece. To protect the electronics from bodily fluids and assure materials biocompatibility, the electronics may be encapsulated into the mouthpiece during the casting or molding process of the mouth piece.

The instrumentation inside the oral cavity should be wireless. At todays standard of technology, it would not be acceptable to use cables through the mouth to connect to the data logger or a power supply. Therefore, the electronics should either be battery-operated or be powered by energy-harvesting of external fields.

The system properties may feature continuous parameter readout in real-time and smallest possible size of the interior electronics. A patient-worn ear piece is not likely to result in additional discomfort, especially since Bluetooth®-style cell phone attachments are in widespread use and many people are used to wearing them. If an ear piece is present, the size of the interior electronics of the intra-oral insert may be reduced by eliminating the battery and its required charging circuit. Energy may then be harvested with a receiving coil energized by a transmitting coil attached to the ear piece. The receiving coil may be embedded in the intra-oral insert material, thus not requiring any additional space in the oral cavity. The ear piece may be connected to a smart device for continuous data transmission, data logging and display to a remote station. A cable can be connected between the ear piece and the smart device for this connection in order to simplify the electronics of the ear piece whereby minimizing its power consumption and thus its battery size and total physical size and weight.

It is therefore an advantage of the disclosure to provide a dental monitoring system capable of monitoring the physical and biochemical properties within the oral cavity of a patient.

These and other features, aspects, and advantages of the present disclosure will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

Figure 1:
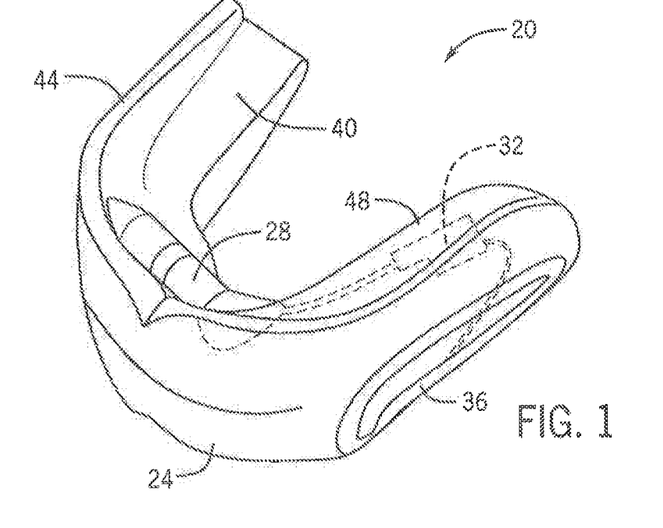
FIG. 1 shows a perspective view of the intra-oral insert of the dental monitoring system.
Figure 2:
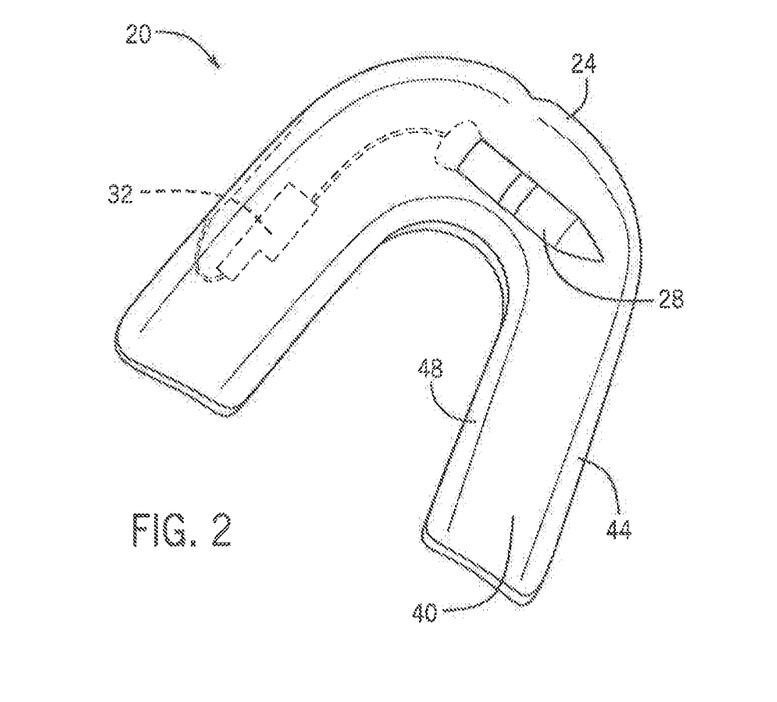
FIG. 2 shows a top view of the intra-oral insert of FIG. 1.
Figure 3:
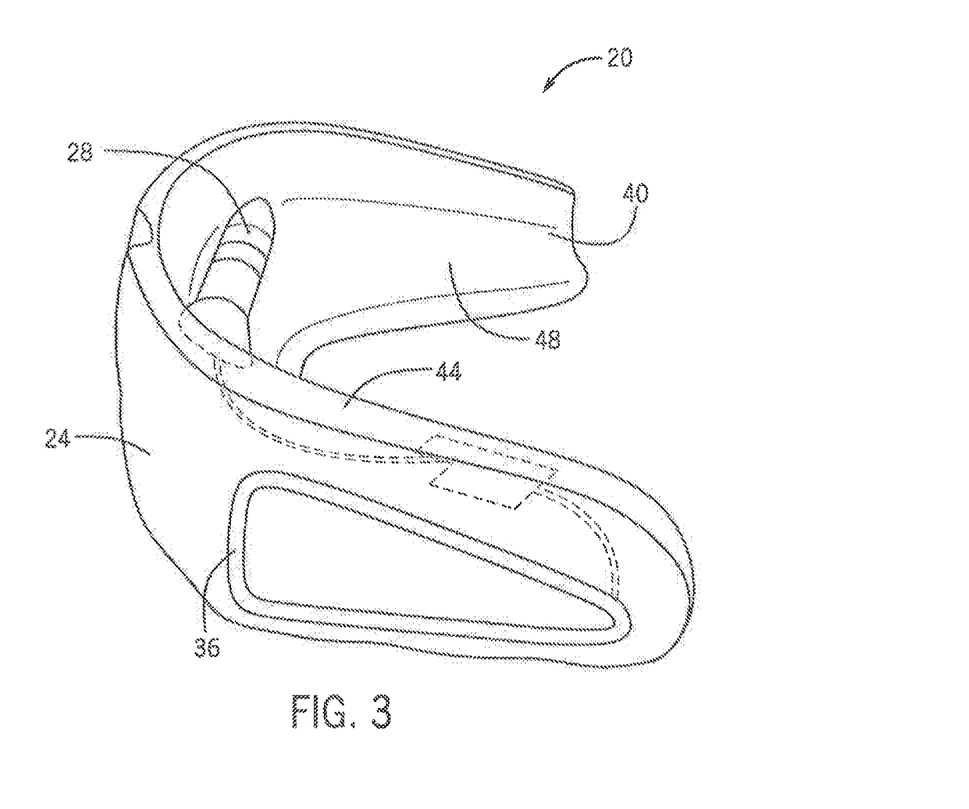
FIG. 3 shows a perspective side view of the intra-oral insert of FIG. 1.

A dental monitoring system 20 for monitoring a variety of subject parameters is provided. FIGS. 1-3 show an intra-oral insert 24 for insertion into the mouth of a subject, which in some embodiments may be a mouth guard or similar device. According to one embodiment, the intra-oral insert 24 may be configured to contain internal components of the dental monitoring system 20. A sensor 28 is connected to and at least partially received in the intra-oral insert 24. The intra-oral insert 24 also contains a controller 32 and a transponder coil 36 within the intra-oral insert 24 such that the controller 32 and the transponder coil 36 are interior to the intra-oral insert 24.

In some embodiments, the intra-oral insert 24 may be configured to be received in the mouth of a subject and contain components of the dental monitoring system 20. As depicted in FIGS. 1-3, the intra-oral insert 24 may be U-shaped having an inner recessed area 40 disposed between a raised outer profile 44 and a raised inner profile 48. In some embodiments, the raised outer profile 44 can be larger than the raised inner profile 48. The raised outer profile 44 and the raised inner profile 48 may be tapered such that an anterior end of the intra-oral insert 24 has a larger raised outer profile 44 and raised inner profile 48 than a posterior end of the intra-oral insert 24. The intra-oral insert 24 may be dimensioned in order to facilitate a comfortable fit around the maxillary teeth of the subject. In other embodiments, the intra-oral insert 24 may be dimensioned in order to facilitate a comfortable fit around the mandibular teeth of the subject. The intra-oral insert 24 is configured to contain the controller 32 and a transponder coil 36 within the intra-oral insert 24 such that the controller 32 and the transponder coil 36 are interior to the intra-oral insert 24.

The intra oral insert 24 can be received or implanted on the Mandibular or Maxillary levels of the subject. Additionally, attachments and inserts can be positioned on the buccal (cheek) or lingual (tongue) side of the alveolar margin.

In some embodiments, the sensor 28 is configured to monitor at least one dental parameter of the subject. The sensor 28 may be fixed to the intra-oral insert 24 such that the sensor is positioned near a bottom curved portion of the U-shaped intra-oral insert 24 over a top surface of the inner recessed area 40 of the intra-oral insert 24. The sensor 28 can at least partially extend outside of the intra-oral insert 24 such that the sensor 28 can directly interface with the environment of the oral cavity of the subject and come in contact with bodily fluids or gases therein or come in contact with teeth, for example to measure bite pressure and teeth grinding. The sensor 28 may be generally cylindrical in shape with a conical end structure positioned such that the conical end surface directly interfaces with the oral cavity of the subject. The sensor 28 may be in direct or wireless electrical communication with at least one of the controller 32 or the transponder coil 36. In one embodiment, the sensor may be a pH sensor configured to measure the pH level in the subject's oral cavity. In other embodiments, the sensor 28 can be a temperature sensor, a pressure sensor, a moisture sensor, a light sensor, total dissolved solids, ionic strength, conductivity, dissolved oxygen, oxidation-reduction potential or any combination of sensors. In yet other embodiments, the parameter can be the sensing of a biochemical species, such as with an ion-selective chem-FET (chemical field effect transistor). Additional non-limiting examples of parameters that can be measured by sensor 28 include: normal force, shear force, pressure, acceleration, velocity, and temperature.

The transponder coil 36 may be positioned near an exterior surface of the intra-oral insert 24 in order to facilitate wireless communication in the dental monitoring system 20. The transponder coil 36 may be embedded in a side wall of the raised outer profile 44 of the intra-oral insert 24 such that when the intra-oral insert 24 is inserted into a subject's mouth, the transceiver coil is positioned adjacent to an inner surface of the subject's cheek. In some embodiments, the transponder coil 36 may be triangular in shape and may extend along the length of the side wall of the intra-oral insert 24. The transponder coil may be wound from litz wire, which makes the coil flexible to make the intra-oral insert more pliable so it may conform better to the oral cavity and mouth movements for increased wearing comfort for the subject. The transponder coil 36 may be in direct or wireless electrical communication with at least one of the sensor 28 or the controller 32.

Figure 7:
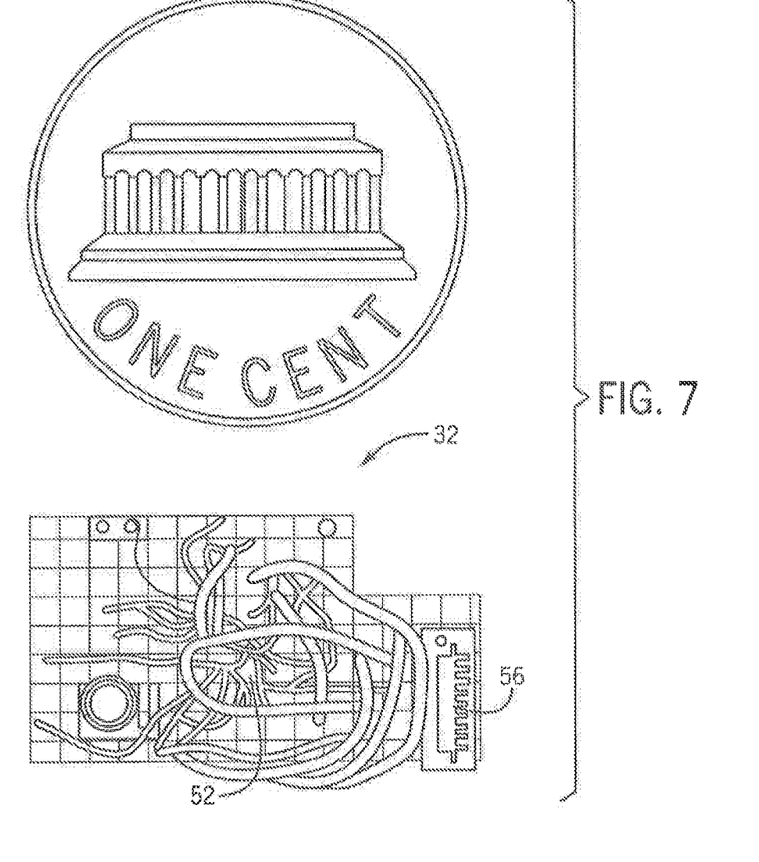
FIG. 7 shows, at the bottom, a top view of the controller of the dental monitoring system.
Figure 8:
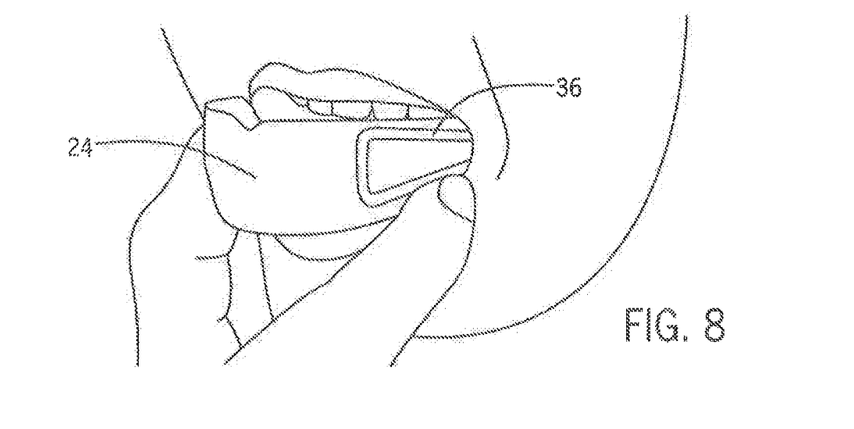
FIG. 8 shows an environmental view of the intra-oral insert of the dental monitoring system during insertion into the mouth of a subject.

Referring now to FIGS. 1-4 and 8, one embodiment of the controller may be configured to control wireless communication within the dental monitoring system 20. In some embodiments, the controller can be embedded below the inner recessed area 40 and positioned on the same side of the intra-oral insert 24 as the transponder coil 36. The controller may be in direct or wireless electrical communication with at least one of the sensor 28 or the transponder coil 36. In some embodiments, the controller 32 comprises a microcontroller chip 52 and a programming port 56. The programming port may be a JTAG programming port. The controller 32 may feature a non-volatile memory configured to allow for storage of data acquired by the sensor 28 or transmission of data acquired by the sensor 28 to the transponder coil 36. The controller 32 provides the intra-oral insert 24 the ability to transmit data from the intra-oral insert through the dental monitoring system 20 using near-field communication. The electronic circuit may incorporate a supercapacitor or a small primary or re-chargeable battery to store a certain amount of energy to operate temporarily without being energized through the transceiver coil. A non-limiting example of the size of the controller 32 is shown in FIG. 7 where the controller 32 is compared to the size of a United States penny.

Figure 4:
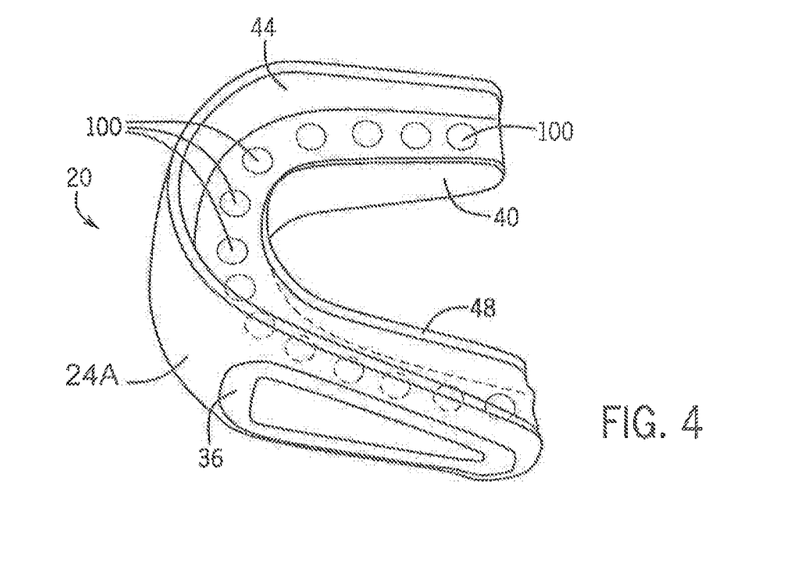
FIG. 4 shows a perspective top and side view of another intra-oral insert according to this disclosure.

FIG. 4 shows a perspective top and side view of another intra-oral insert 24A according to this disclosure. The intra oral insert 24A shown in FIG. 4 includes a plurality of pressure sensors 100 positioned on or in the inner recessed area 40 disposed between the raised outer profile 44 and the raised inner profile 48.

One non-limiting example of pressure sensors 100 that could be implemented into the intra-oral insert 24A to measure teeth grinding pressure and timing during sleep of a subject. Since the pressure sensors 100 are placed in the bite area of a subject, which generally corresponds with the inner recessed area 40 disposed between the raised outer profile 44 and the raised inner profile 48, when the subject grinds their teeth, pressure is exerted on the pressure sensors 100 and the signals change. By having a plurality of pressure sensors 100, it is possible to determine the distribution of teeth grinding load and thus recommend an intervention. The pressure sensors 100 can be embedded in the substrate of the intra-oral insert 24A which holds the components of the oral sensor. The pressure sensors 100 can be embedded in such a way as to be flush with a surface of the inner recessed area 40 of the intra-oral insert 24A which increases the wear comfort for the subject. The pressure sensors 100 can be made from elastomeric material such that while pressure sensing the pressure sensors 100 can conform to the crowns of the teeth, minimizing discomfort for the subject and providing a more accurate pressure measurement. The sensors may be configured to measure lateral movement of the teeth in addition to axial movement for a more complete, possibly 3-dimensional, analysis of the teeth grinding movement.

Figure 5:
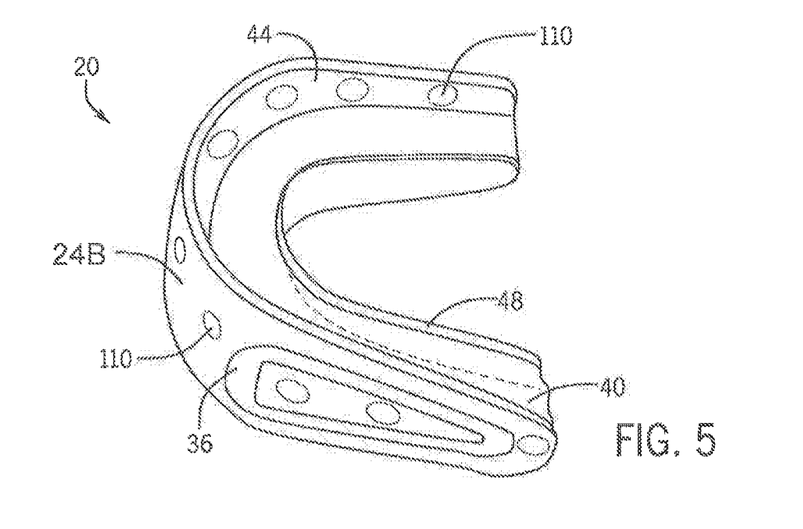
FIG. 5 shows a perspective top and side view of yet another intra-oral insert according to this disclosure.

FIG. 5 shows a perspective top and side view of another intra-oral insert 24B according to this disclosure. A plurality of biochemical sensors 110 are shown to be placed on both sides of the raised outer profile 44 of the intra-oral insert 24B. By placing the biochemical sensors 110 on both sides of the raised outer profile 44 of the H-profile of the intra-oral insert 24B, the sensors are predominantly exposed to either the gum side or the mouth cavity wall. It is advantageous to measure for biochemical species in a variety of locations inside the mouth cavity because the biochemical species are not always evenly distributed. Moreover, the distribution itself is helpful in diagnosing the health status of the oral cavity.

The biochemical sensors 110 are capable of generating a signal according to the presence of certain chemicals in the saliva of the subject. One non-limiting example of biochemical sensors that can be used are ISFET (ion-sensitive field-effect transistor) sensors, which comprise a preferred configuration where there is a functional boundary between the wet biochemical side of the saliva media and the dry semiconductor electronic side that generates the electrical signal. The functional boundary may be an inert layer of insulating gate material, such as silicon dioxide. This configuration yields a dimensionally small and mechanically and biochemically rugged sensor. Moreover, it operates with minimal current, making it ideal for ultra-low power applications such as desirable and advantageous for the oral sensor.

Figure 6:
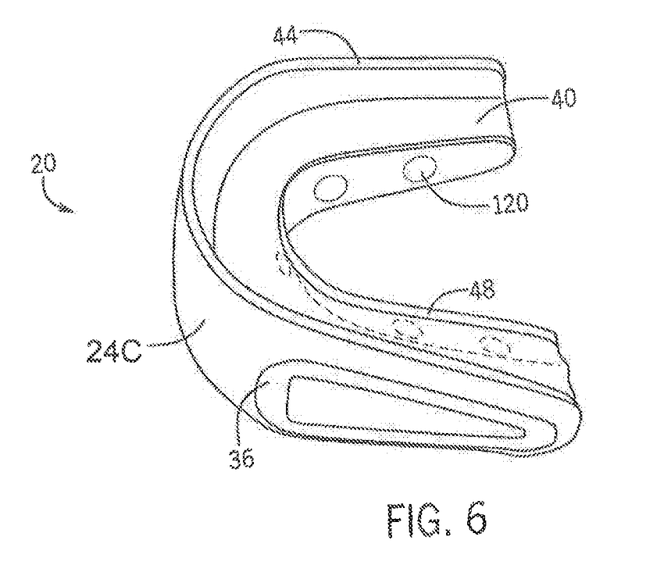
FIG. 6 shows a perspective top and side view of still another intra-oral insert according to this disclosure.

FIG. 6 shows a perspective top and side view of another intra-oral insert 24C according to this disclosure having biochemical sensors 120 placed around the raised inner profile 48 of the intra-oral insert. The placement of biochemical sensors 120 provides access to the saliva area near the tongue so that the biochemical content of that area may be measured. By placing the biochemical sensors 120 on the inner side of the inner raised inner profile 48 of the H-profile of the intra-oral insert 24C, the biochemical sensors 120 will be exposed to the surface of the tongue of the subject. Since the tongue's surface carries a wealth of medically relevant information, these sensors will yield valuable information for medical diagnoses. In one example, the biochemical sensors 120 can analyze biomarkers or other proteins and protein derivatives of the subject.

Figure 9:
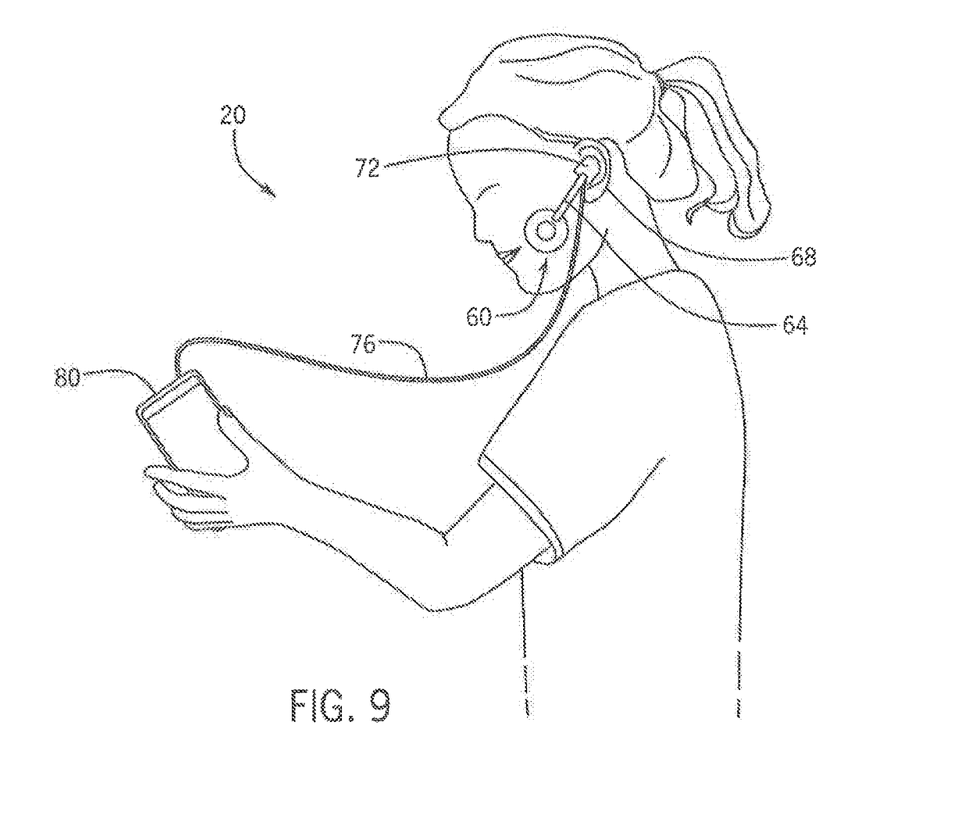
FIG. 9 shows a side view of the dental monitoring system on a subject.
Figure 10:
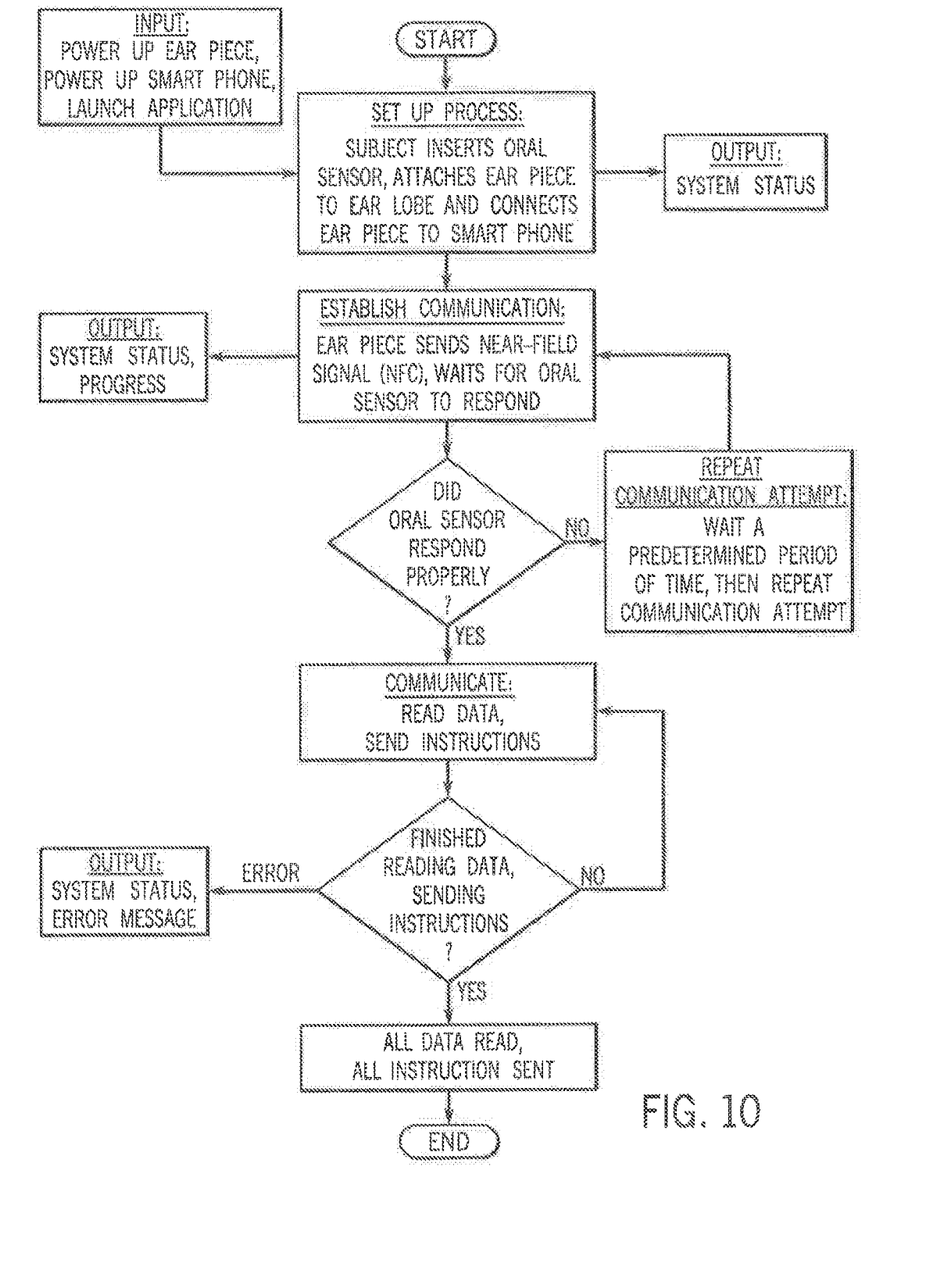
FIG. 10 shows a flow diagram that illustrates the application, initialization and operation of the dental monitoring system according to the disclosure.
Figure 11:
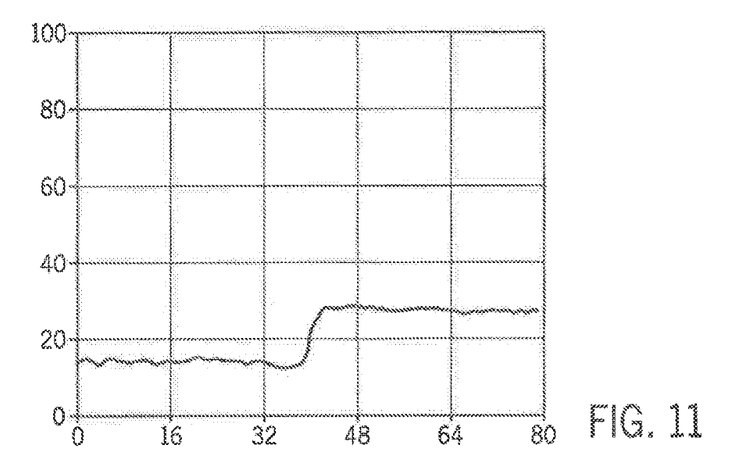
FIG. 11 shows the results of a case study of the dental monitoring system in response to an added acidic buffer.
Figure 12:
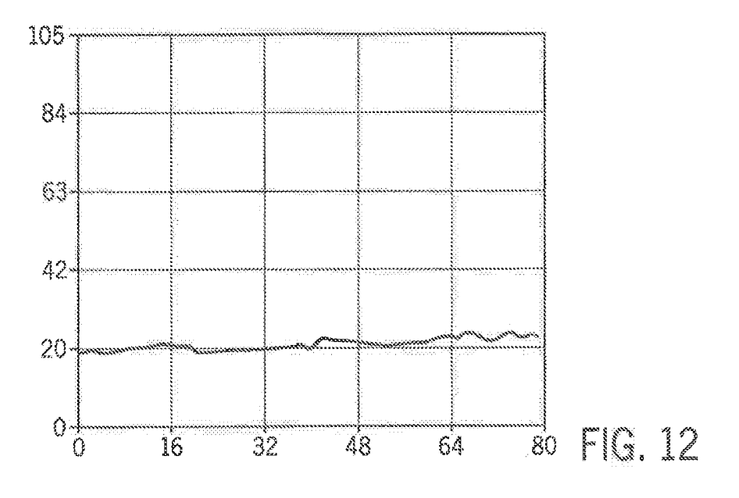
FIG. 12 shows the results of a case study of the dental monitoring system in response to an added neutral buffer.

FIGS. 9 and 10 show the dental monitoring system 20 where the intra-oral insert 24 may wirelessly communicate with a transceiver coil 60 positioned outside of the subject's mouth. In some embodiments, the intra-oral insert 24 is inserted in the mouth of a subject and may be secured around the maxillary teeth of the subject. Once inserted into the mouth of the subject, the sensor 28 may directly interface with the environment inside the mouth of the subject and any fluids or gases that may be present in the mouth of the subject. The sensor 28 may electrically communicate the data monitored by the sensor 28 with the controller 32. The data may be electrically communicated between the sensor 28 and the controller 32 via wired connection or wireless connection. The controller 32 can temporarily store or automatically transmit the data received from the sensor 28 to the transponder coil 36. The transponder coil 36 may communicate the data received from the controller 32 wirelessly with the transceiver coil 60. The wireless communication may be encrypted for data security. While FIG. 9 illustrates use of the intra-oral insert 24 in the dental monitoring system 20, any of the intra-oral inserts 24A, 24B, 24C may be used in the dental monitoring system 20.

The transceiver coil 60 may be positioned outside of the subject's mouth adjacent to an outer surface of the subject's cheek. In some embodiments, the transceiver coil 60 may be positioned to oppose the transponder coil 36 such that the transceiver coil 60 and the transponder coil 36 are directly across the subject's cheek. In some embodiments, the transceiver coil 60 may be circular in shape and may feature a central opening. One skilled in the art would appreciate that the transceiver coil can take any appropriate shape in order to facilitate wireless communication between the transceiver coil 60 and the transponder coil 36.

The transceiver coil 60 may be mounted to a support frame 64 that is dimensioned to position the transceiver coil 60 such that it can wirelessly communicate with the transponder coil 36. In some embodiments, the support frame may extend from an ear hook 68 to the transceiver coil 60 along an outer surface of the subject's cheek. The ear hook 68 can loop around at least a portion of an ear of the subject to secure the position of the support frame 64 and consequently the transceiver coil 60. The ear hook 68 may have a central body 72 that the support frame 64 can extend from. In some embodiments, the central body 72 can be a wirelessly connected device such as a Bluetooth™ connected device or a Wi-Fi™ connected device, Another non-limiting example of the wireless protocol for transmitting data from the transceiver coil includes using a wireless medical band signal (MICS—Medical Implant Communication Service) at 402-405 MHz. The wireless communication may be encrypted for data security.

In other embodiments, the central body 72 can be connected via a wire 76 to a smart device 80. The smart device 80 can store, process, analyze, transmit and display the data acquired by the dental monitoring system 20.

In still other embodiments, the external transceiver, instead of an earpiece can be a padded patch-like embodiment, which can be attached to the cheek with an adhesive. This enables a longer term (such as overnight) data logging from the oral cavity, bring the transceiver coil closer to the transponder coil and fix it in an optimal location for maximum energy transfer.

The dental monitoring system 20 can wirelessly communicate from the transponder coil 36 to the transceiver coil 60 using near-field communication. Near-field communication (NFC) between the transponder coil 36 and the transceiver coil 60 requires the transponder coil 36 and the transceiver coil 60 to be positioned near each other on opposing sides of the subject's cheek.

NFC is a short-range radio frequency (RF) communication technology that can operate at a distance of up to 10 cm or less between two communicating devices. Communication via NFC involves an initiator device (often referred to as a "reader") and a target device. The initiator device may be the transceiver coil 60 and the target device can be the transponder coil 36.

In some embodiments, the transceiver coil 60 can generate an RF field that can power the transponder coil 36, which in turn supplies the controller 32 with sufficient power such that it does not require batteries or a power source embedded in the intra-oral insert 24. In this configuration, the transponder coil 36 may be read-only and directed to a single application, for example, identification of the transceiver coil 60 and transmission of data associated with the sensor 28, for example through impedance modulation. In this configuration, the intra-oral insert 24 may be operable to communicate via NFC without onboard power thereby reducing the size of the electronics required in the intra-oral insert 24 as well as increasing the amount of time the intra-oral insert 24 can remain in the subject.

In some embodiments, processing electronics inside the patient's body must transmit data wirelessly to suitable readout electronics outside the body to display, analyze or log the signals acquired by the sensor 28. In order to minimize the size of the interior electronics of the intra-oral insert 24, the available power, either through a battery, a supercapacitor or through an energy-harvesting element, can be small, necessitating low-power or even ultralow-power devices. In a non-limiting example, these devices can transmit at very low power such that their range will be short as well, possibly 0.5 to 10 inches. As a result, an "interrogating" or "listening" device such as the transceiver coil 60 must be placed within 0.5 to 10 inches of the transponder coil 36 in the intra-oral insert 24, preferably on or near the cheek of the subject. The short communication distance may inherently serve data security, even without encryption, because any intercepting device would have to be brought within close range to the subject.

Two non-limiting embodiments of data readout that may be accomplished, continuous readout and batch readout, each having its distinct advantages as explained below.

Continuous data readout can require the transceiver coil 60 to be "listening" at all times to receive data from the transponder coil 36 in real-time. Since the transceiver coil 60 must be physically close to the transponder coil 36 at all times, it would have to be worn by the subject for the duration of the data collection. Such a receiver could be built in the form of the ear hook 68 with the transceiver coil 60 receiving element mounted to a support frame 64 extending to the cheek near the transponder coil 36. The ear hook 68 may have much less stringent space limitations and can therefore incorporate a large enough battery, super capacitor or other power source to either relay the data in real-time to a nearby data display/logger or store the data for batch download at a later time. Continuous data readout may allow the data to be read by a dental practitioner in real-time, intervening quickly as certain situations arise. Alarms may be programmed in case certain parameters go out of range. The interior circuits may be powered by energy-harvesting techniques, thereby eliminating the need for a battery and reducing the size of interior electronics required in the intra-oral insert 24.

Batch data readout can allow the interior electronics of the intra-oral insert 24 to store the acquired data in an on-board flash memory to be retrieved at a later time. In this configuration, the interior electronics may be fitted with a battery or super capacitor because the circuits can operate without an external energy source. The interior electronics can be programmed to mostly stay in an ultra-low power sleep state, wake up briefly at periodic times, measure sensor signals, store the data in its memory and return to the ultra-low power sleep state. This scheme may significantly increase the time the interior electronics could monitor sensor signals autonomously. In some embodiments the wake-up may be triggered by certain conditions arising from certain sensor signals. Readout can be accomplished periodically with the transceiver coil 60 being briefly placed near the cheek of the patient during data download and simultaneous recharging of the battery or super capacitor. In this embodiment of batch data readout, the subject is not required to wear an ear hook 68 in order to maintain communication between the transponder coil 36 and the transceiver coil 60.

FIG. 10 shows a flow diagram that illustrates the application, initialization and operation of the dental monitoring system according to the disclosure. FIG. 10 begins with the subject inserting the intra-oral insert 24 (or any of the intra-oral inserts 24A, 24B, 24C) and attaching the ear hook 68. The subject then connects the ear hook 68 and/or the central body 72 to the smart device 80. On the smart device 80 an application is launched, which initiates the communication via the near-field communication (NFC) protocol. Once communication is established, instruction commands are sent to the intra oral insert 24 and data is read from it. Status messages, error messages and data are processed and displayed on a graphical user interface with which the subject can interact. The controller may be configured to communicate a command to the plurality of sensors to generate a data reading, the controller communicates the data reading to a smart device configured to process and display the data reading on a graphical user interface.

The dental monitoring system 20 may have an associated method of use. The method of dental monitoring can include the steps of: (i) inserting the intra-oral insert 24 (or any of the intra-oral inserts 24A, 24B, 24C) into the mouth of a subject; (ii) sensing a parameter of the subject using a sensor 28 connected to the intra-oral insert 24; (iii) communicating the sensed parameter to a controller 32 having a non-volatile memory; (iv) communicating the sensed parameter from the controller 32 to a transponder coil 36 received in the intra-oral insert 24; and (v) communicating the sensed parameter wirelessly from the transponder coil 36 to a transceiver coil 60 using near-field communication. In some embodiments, the parameter of the subject is sensed when the subject initiates a force to the sensor 28. The parameter of the subject can be a pH. In other embodiments, the parameter can be a temperature, pressure, moisture, light, total dissolved solids, ionic strength, conductivity, dissolved oxygen, oxidation-reduction potential or any combination of parameters. In still other embodiments, the parameter can be the sensing of the presence and concentration of a chemical species with, for example, a chem-FET (chemical field-effect transistor).

A non-limiting example of prototype development involved Texas Instruments' semiconductors for NFC. The prototype can use the international NFC protocol ISO/IEC 15693 operating at a frequency of 13.56 MHz. The interior electronics can use a transponder that operates without a battery and is powered only by RF energy harvested by a small transponder coil from a small transceiver coil. The transceiver coil is mounted near the cheek of a subject and is driven by an NFC transceiver. Communication to the transponder coil can be facilitated by modulation of the carrier frequency and communication back to the transceiver coil can be facilitated by the transponder changing the impedance of the transponder coil by partially shorting it out. This requires a low amount of energy on the transponder coil side but the impedance changes can be sensed by the transceiver circuit. Thus a bi-directional communication is possible without the transponder having to actively transmit energy and thereby minimizing energy requirements to the point where not even a battery is required and all needed energy is harvested by the transponder coil energized by the transceiver coil.

The coils and hardware used in the prototype were manufactured by Texas Instruments and belong to the RF430 family of NFC devices. An evaluation development kit was purchased containing the TRF7970A NFC Reader (transceiver coil) and the RF430FRL15EVM tag (transponder coil). Initial tests showed that the system and their devices were suitable for the prototype. While the NFC Reader (transceiver coil) was kept as is, the NFC tag (transponder coil) was designed from scratch to be fitted into an intra-oral insert and connected to sensors relevant for oral cavity monitoring. The NFC tag is a transponder coil and is energized by the RF energy transmitted by the NFC Reader which energizes the transceiver coil. Data transfer is bi-directional. The NFC tag (transponder coil) does not need a battery.

A non-limiting proof of concept was performed by placing the intra-oral insert 24 prototype in a water beaker, simulating the wet environment of the oral cavity, and placing the prototype reader board just outside the beaker. In this prototype configuration, the reader board is part of the Texas Instruments development kit and is meant as a demonstration of the system. The reader coil may be as far as two inches from the receiver coil, although improved communication was achieved at a distance of one inch. The mouth piece was immersed under water in the beaker and held down by a weight to prevent it from floating. The reader coil is approximately 1 inch from the receiver coil of the tag. Since the radio frequency had to penetrate at least ¼" of water, the system demonstrated that the soft tissue of a cheek would not be an impediment to the operation.

Figure 13:
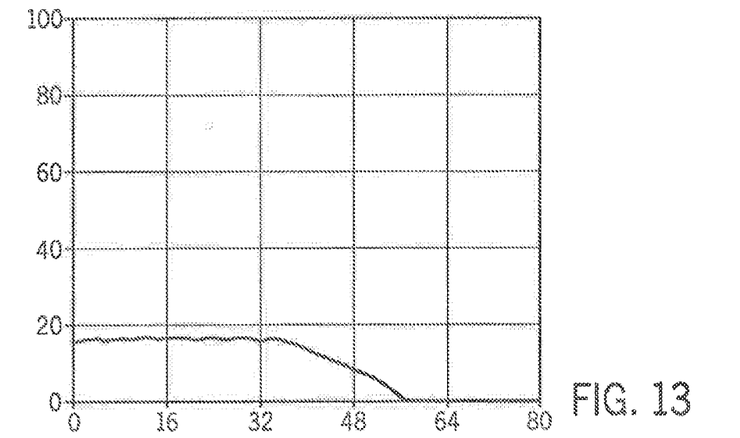
FIG. 13 shows the results of a case study of the dental monitoring system in response to an added basic buffer.
Figure 14:
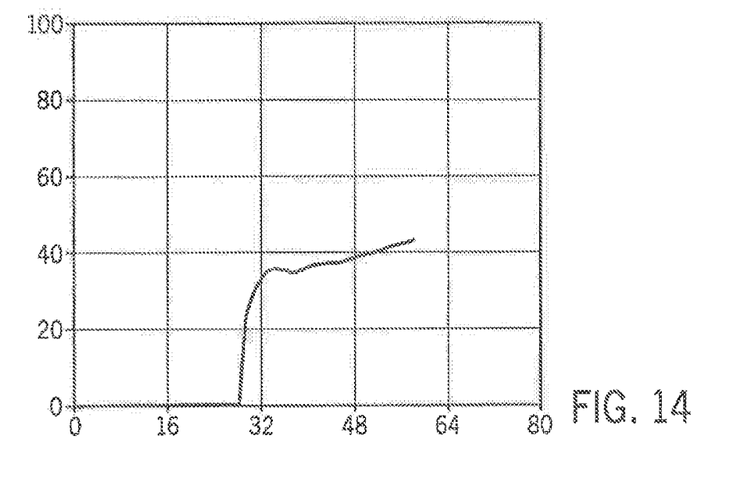
FIG. 14 shows the results of a case study of the dental monitoring system of FIG. 13 in response to an added pH 4 buffer.

To demonstrate the proof-of-concept, a single pH sensor was chosen. The sensor was an electrochemical cell made from dissimilar metals that act as a weak electro-motive force generator outputting a small current proportional to the number of ions and their polarity in the water, which can correlate to a measure of the pH value. FIG. 11 through FIG. 14 show data acquired in real-time, one data point per second, with the abscissa being the time axis and the ordinate plotting the sensor response in arbitrary units. As can be seen, when starting with tap water, which is roughly neutral, the graph jumps up when acidic buffer is added (FIG. 11), stays approximately the same when neutral buffer is added (FIG. 12), and drops when basic buffer is added (FIG. 13). Adding basic buffer resulted in reaching the lower end of the scale at "0". The "un-pegging" of the sensor response through the addition of acidic buffer is shown in FIG. 13. This data is the only one that did not start with fresh tap water. FIG. 14 shows the pH sensor response to tap water from FIG. 13 and a squirt of pH-10 buffer from the previous Figure and then after a squirt of pH-4 buffer was added at the "28" mark to bring the sensor response up from its peg.

Thus, the disclosure provides a dental monitoring system capable of monitoring the physical and biochemical properties within the oral cavity of a patient.

Although the disclosure has been described in considerable detail with reference to certain embodiments, one skilled in the art will appreciate that the present disclosure can be practiced by other than the described embodiments, which have been presented for purposes of illustration and not of limitation. Therefore, the scope of the appended claims should not be limited to the description of the embodiments contained herein.

What is claimed is:

1. A dental monitoring system comprising:
an intra-oral insert configured to be received in a mouth of a subject, wherein the intra-oral insert does not include a battery, wherein the intra-oral insert does not include a charging circuit;
one or more sensors connected to the intra-oral insert and in electrical communication with a controller having a non-volatile memory;
a near-field communication transponder coil received in the intra-oral insert and in electrical communication with the controller; and
a near-field communication transceiver coil in selective wireless electrical communication with the transponder coil, the transceiver coil selectively powering the transponder coil;
wherein the selective wireless communication between the transponder coil and the transceiver coil is provided by near-field communication,
wherein the near-field communication communicates power from the transceiver coil to the transponder coil, and
wherein the power is harvested by the transponder coil that is energized by the transceiver coil.

2. The dental monitoring system of claim 1 further comprising:
a support frame configured to mount the transceiver coil.

3. The dental monitoring system of claim 2 wherein:
the support frame is structured to loop around at least a portion of an ear of the subject.

4. The dental monitoring system of claim 3 wherein:
the support frame is dimensioned such that the transceiver coil is adapted or configured to be positioned adjacent to a cheek of the subject, and
the transceiver coil is positioned to oppose the transponder coil such that the transceiver coil and the transponder coil are adapted or configured to be positioned directly across the cheek of the subject.

5. The dental monitoring system of claim 1 further comprising:
an adhesive patch that retains the transceiver coil on a cheek of the subject.

6. The dental monitoring system of claim 5 wherein:
the adhesive patch can be worn for a period of time thereby providing continuous monitoring over the period of time.

7. The dental monitoring system of claim 1 wherein:
at least one of the one or more sensors is a biochemical sensor.

8. The dental monitoring system of claim 1 wherein:
at least one of the one or more sensors is a pressure sensor.

9. The dental monitoring system of claim 1 wherein:
at least one of the one or more sensors is a pH sensor.

10. The dental monitoring system of claim 1 wherein:
at least one of the one or more sensors is a biochemical sensor and at least one of the one or more sensors is a pressure sensor.

11. The dental monitoring system of claim 1 wherein:
the one or more sensors are positioned on an inner recessed area disposed between a raised outer profile and a raised inner profile of the intra-oral insert.

12. The dental monitoring system of claim 1 wherein:
the one or more sensors are positioned on both sides of a raised outer profile that extends from an inner recessed area disposed between a raised inner profile and the raised outer profile of the intra-oral insert.

13. The dental monitoring system of claim 1 wherein:
the one or more sensors are positioned on a raised inner profile that extends from an inner recessed area disposed between the raised inner profile and a raised outer profile of the intra-oral insert.

14. The dental monitoring system of claim 1 wherein:
the controller comprises a microcontroller and a Joint Test Action Group (JTAG) programming port.

15. The dental monitoring system of claim 1 wherein:
the near-field communication communicates data from the transceiver coil to the transponder coil.

16. The dental monitoring system of claim 1 wherein:
the near-field communication communicates data from the transponder coil to the transceiver coil.

17. A dental monitoring system comprising:
an intra-oral insert configured to be received in a mouth of a subject, wherein the intra-oral insert does not include a battery, wherein the intra-oral insert does not include a charging circuit;
a plurality of sensors connected to the intra-oral insert and in electrical communication with a controller having a non-volatile memory, the plurality of sensors configured to monitor one or more parameters of pressure, force, shear force, acceleration, light, moisture, velocity, pH, and temperature;
a near-field communication transponder coil received in the intra-oral insert and in electrical communication with the controller; and
a near-field communication transceiver coil in selective wireless electrical communication with the transponder coil, the transceiver coil selectively powering the transponder coil, the selective wireless communication between the transponder coil and the transceiver coil is provided by near-field communication facilitating bi-directional data communication while simultaneously powering transponder circuitry through energy harvesting;
the controller being configured to communicate a command to the plurality of sensors to generate a data reading, the controller communicating the data reading to a smart device configured to process, analyze and store the data reading and display the data reading on a graphical user interface,
wherein the near-field communication communicates power from the transceiver coil to the transponder coil, and
wherein the power is harvested by the transponder coil that is energized by the transceiver coil.

18. A method of dental monitoring, the method comprising:

inserting an intra-oral insert into a mouth of a subject, wherein the intra-oral insert does not include a battery, wherein the intra-oral insert does not include a charging circuit;

sensing a parameter of the subject using a sensor connected to the intra-oral insert:

communicating the sensed parameter to a controller having a non-volatile memory;

communicating the sensed parameter from the controller to a near-field communication transponder coil received in the intra-oral insert;

communicating the sensed parameter wirelessly from the transponder coil to a near-field communication transceiver coil using near-field communication, wherein the near-field communication communicates power from the transceiver coil to the transponder coil, wherein the power is harvested by the transponder coil that is energized by the transceiver coil; and communicating from the transceiver coil to the transponder coil commands that change the transponder's coil operation.

19. The method of dental monitoring of claim 18, wherein:
the sensed parameter of the subject is sensed when the subject initiates a force to the sensor.

20. The method of dental monitoring of claim 18, wherein:
the sensed parameter of the subject is sensed by the sensor and exceeds a pre-determined trigger threshold.

21. The method of dental monitoring of claim 18, wherein:
the sensed parameter of the subject is pH.

22. The method of dental monitoring of claim 18, wherein:
the sensed parameter of the subject is pressure.

23. A method of wireless intraoral monitoring, the method comprising:

inserting an intra-oral insert into a mouth of a subject, wherein the intra-oral insert does not include a battery, wherein the intra-oral insert does not include a charging circuit;

sensing a parameter of the subject using a sensor connected to the intra-oral insert, the parameter at least one of a physical or biochemical parameter:

communicating the sensed parameter to a controller having a non-volatile memory;

communicating the sensed parameter from the controller to a near-field communication transponder coil received in the intra-oral insert;

communicating the sensed parameter wirelessly from the transponder coil to a near-field communication communicates power from the transceiver coil to the transponder coil, wherein the power is harvested by the transponder coil that is energized by the transceiver coil; and communicating from the transceiver coil to the transponder coil commands that change the transponder's coil operation.

* * * * *

UNITED STATES PATENT AND TRADEMARK OFFICE
CERTIFICATE OF CORRECTION

| | | |
|---|---|---|
| PATENT NO. | : 11,963,839 B2 | |
| APPLICATION NO. | : 16/060667 | |
| DATED | : April 23, 2024 | |
| INVENTOR(S) | : Inder Raj S. Makin et al. | |

It is certified that error appears in the above-identified patent and that said Letters Patent is hereby corrected as shown below:

In the Claims

Claim 23, Column 14, Line 22, "communication communicates" should be --communication transceiver coil using near-field communication, wherein the near-field communication--.

Signed and Sealed this
Eighteenth Day of June, 2024

Katherine Kelly Vidal
*Director of the United States Patent and Trademark Office*